United States Patent [19]

König et al.

[11] Patent Number: 4,613,686
[45] Date of Patent: Sep. 23, 1986

[54] PROCESS FOR THE PREPARATION OF POLYISOCYANATES WITH BIURET STRUCTURE

[75] Inventors: Klaus König, Leverkusen; Josef Pedain, Cologne; Helmut Woynar, Dormagen, all of Fed. Rep. of Germany

[73] Assignee: Bayer Aktiengesellschaft, Leverkusen, Fed. Rep. of Germany

[21] Appl. No.: 695,138

[22] Filed: Jan. 25, 1985

[30] Foreign Application Priority Data

Jan. 31, 1984 [DE] Fed. Rep. of Germany ....... 3403277

[51] Int. Cl.$^4$ ........................................... C07C 127/24
[52] U.S. Cl. ..................................... 560/335; 564/38
[58] Field of Search .................... 564/38; 260/453 AB

[56] References Cited

U.S. PATENT DOCUMENTS

| | | |
|---|---|---|
| 3,124,605 | 3/1964 | Wagner ............................... 260/453 |
| 3,284,479 | 11/1966 | Windemuth et al. ................ 260/453 |
| 3,350,438 | 10/1967 | Hennig ............................... 260/453 |
| 3,367,956 | 2/1968 | Hennig et al. ....................... 260/453 |
| 3,441,588 | 4/1969 | Wagner et al. ...................... 260/453 |
| 3,462,470 | 8/1969 | Emery et al. ....................... 260/453 |
| 3,526,652 | 9/1970 | Powers ............................... 260/453 |
| 3,824,266 | 7/1964 | Dietrich et al. ............. 260/453 AB |
| 3,862,973 | 1/1975 | Dietrich et al. ............. 260/453 AB |
| 3,896,154 | 7/1975 | Takahashi et al. ............. 260/453 P |
| 3,903,126 | 9/1975 | Woerner et al. ............. 260/453 AB |
| 3,954,825 | 5/1976 | Touhey, Jr. et al. ......... 260/453 AB |
| 3,976,622 | 8/1976 | Wagner et al. ............. 260/77.5 AT |
| 4,051,165 | 9/1977 | Wagner et al. ............. 260/453 AB |
| 4,147,714 | 4/1979 | Hetzel et al. ................. 260/453 AB |
| 4,176,132 | 11/1979 | Ide et al. ......................... 260/453 A |
| 4,192,936 | 3/1980 | Mohring et al. ..................... 528/59 |
| 4,218,390 | 8/1980 | Brusilovsky et al. ........ 260/453 AB |
| 4,264,519 | 4/1981 | Hennig et al. .............. 260/453 AB |
| 4,290,969 | 9/1981 | Komatsu et al. ............. 260/453 A |
| 4,292,255 | 9/1981 | Hennig et al. .............. 260/453 AR |
| 4,320,068 | 3/1982 | Schwindt et al. ............ 260/453 AB |
| 4,377,644 | 3/1983 | Kopp et al. ............................ 521/94 |
| 4,386,218 | 5/1983 | Rasshofer et al. ..................... 564/38 |
| 4,525,590 | 6/1985 | Rasshofer et al. ..................... 564/38 |
| 4,532,266 | 7/1985 | Rasshofer et al. ..................... 564/38 |
| 4,532,317 | 7/1985 | Rasshofer ............................... 564/38 |

FOREIGN PATENT DOCUMENTS

| | | |
|---|---|---|
| 883504 | 6/1953 | Fed. Rep. of Germany . |
| 1570632 | 10/1973 | Fed. Rep. of Germany . |
| 140744 | 3/1980 | Fed. Rep. of Germany . |
| 889050 | 2/1962 | United Kingdom . |
| 1043672 | 9/1966 | United Kingdom . |
| 1044932 | 10/1966 | United Kingdom . |
| 1263609 | 2/1972 | United Kingdom . |

OTHER PUBLICATIONS

"Pur-Anstrichostoffe"-Haputverhandes der deutschen gewerblichen Berufsgenossenschaft.
"Polyurethane Report"-Paintmakers Association of G.B. Ltd.
Angew. Chemie 72, p. 1002.

Primary Examiner—Charles F. Warren
Assistant Examiner—R. A. Picard
Attorney, Agent, or Firm—Gene Harsh; Joseph C. Gil; Thomas W. Roy

[57] ABSTRACT

The present invention relates to a process for the preparation of polyisocyanates which have a biuret structure of reacting excess quantities of aliphatic diisocyanates with biuretizing agents at elevated temperature, characterized in that the biuretizing agent contains (a) α,α,α-trisubstituted acetic acids which do not contain isocyanate-reactive groups apart from the carboxyl group, and optionally
(b) water, wherein the molar ratio of biuretizing components (a) to (b) is within the range of from 1:0 to 1:2.5.

8 Claims, No Drawings

PROCESS FOR THE PREPARATION OF POLYISOCYANATES WITH BIURET STRUCTURE

BACKGROUND OF THE INVENTION

1. Field of the Invention

The present invention relates to an improved process for the preparation of polyisocyanates with biuret structure which have excellent color quality and good monomer stability, by the reaction of aliphatic diisocyanates with certain carboxylic acids as biuretizing agent.

2. Description of the Prior Art

Aliphatic polyisocyanates which have a biuret structure, in particular those based on hexamethylene diisocyanate, have achieved worldwide technical importance for the production of lightfast and extremely weather resistant lacquers with high gloss retention. For use in this field, in particular for clear and white-pigmented coatings, the market demands colorless to only slightly colored products. Furthermore, for safe processing it is desirable that the portion of monomeric diisocyanates should be as low as possible and should not increase with prolonged storage. On the basis of toxicological investigation, processing is safe up to a maximum monomeric diisocyanate content of 0.7%, provided the usual protective measures for lacquer processing are observed. The above-mentioned limiting value has found its way into the literature (e.g., Memorandum "PUR-Anstrichstoffe" of the Hauptverhandes der deutschen gewerblichen Berufsgenossenschaft and "Polyurethane Report" of the Paintmakers Association).

Numerous processes have become known in the course of time for the preparation of such polyisocyanates, but they all have special problems and disadvantages and do not, or only incompletely fulfill the above-mentioned requirements of the product. The following processes, for example, have been described:

Synthesis from diisocyanates and water, optionally in the presence of catalysts, see DE-PS No. 1,110,394, DE-OS No. 1,668,377, DE-OS No. 2,308,015, GB-PS No. 889,050, GB-PS No. 1,399,228, DDR-PS No. 140,744;

synthesis from diisocyanates and water in the presence of a solvent or a solvent mixture, see DE-OS No. 2,808,801, DE-OS No. 3,030,655;

synthesis from diisocyanates and water in which the water is brought to reaction in the form of steam, see DE-OS No. 2,918,739:

synthesis from diisocyanates and ammonia or ammonia-water mixtures, optionally in the presence of catalysts, see DE-AS No. 1,227,003:

synthesis from diisocyanates and amine, see DE-PS No. 1,165,580, DE-PS No. 1,174,759, DE-OS No. 1,568,017, DE-OS No. 1,963,190, DE-OS No. 2,010,887, DE-OS No. 2,261,065, DE-AS No. 2,438,258, US-P 3,824,266, DE-AS No. 2,609,995, DE-OS No. 2,803,103, DE-PS No. 883,504, GB-PS No. 1,263,609; see also Angew. Chem. 72, page 1002;

synthesis from diisocyanates and amine/alcohol mixtures, see DE-OS No. 2,654,745:

synthesis from diisocyanates and ω,ω'-diaminopoly ethers, see DE-OS No. 1,570,632, DE-AS No. 1,215,365;

synthesis from diisocyanates and substituted ureas, see DE-PS No. 1,101,394, DE-AS No. 1,227,004:

synthesis from diisocyanates and tertiary alcohols, optionally in the presence of catalysts, see DE-AS No. 1,543,178, DE-AS No. 1,931,055, DE-OS No. 2,308,015;

synthesis from diisocyanates and formic acid (DE-PS No. 1,174,760, DE-OS No. 2,308,015);

synthesis from diisocyanates and aldoximes (DE-OS No. 3,007,679).

Processes in which the diisocyanates are reacted with water are difficult to control on account of the inhomogeneity of the reaction mixture. Firstly, the processes are accompanied by the formation of extremely difficultly soluble polyureas which can only be dissolved by the application of high temperatures over a long period of time, whereby the color of the product is deleteriously affected. Even then, a proportion of these polyureas in some cases remains undissolved as a precipitate which is difficult to filter and must be removed by elaborate procedures before further processing is carried out. Furthermore, because of the volatility of most diisocyanates, deposits of urea are liable to form in the steam chamber of the reaction vessel. This also applies to processes in which water is used in vapor form.

When water is used as biuretizing agent, these deposits can only be avoided if solvents or solvent mixtures are used to homogenize the reaction mixture. These methods have, however, various disadvantages. Firstly, they require the use of large quantities of solvents which must subsequently be removed from the finished product by distillation, and secondly, very specific solvent mixtures of glycol ether acetates and phosphoric acid esters are required for colorless products. Furthermore, these processes require reaction temperatures of at least 140° C. to avoid the intermediate precipitation of insoluble ureas. If such precipitates nevertheless occur, e.g. due to low reaction temperatures, it is necessary to employ temperatures of 160° C. or more, as in the processes using water without solvents, if clear products are to be obtained. These high temperatures increase the occurrence of side reactions and lead to a marked loss in color quality.

Processes may be carried out without solvents if water is released in the course of the reaction from a compound which splits off water. These processes include in particular the technically important process using tert.-butanol as biuretizing agent. This process, however, also requires temperatures of about 180° C., with all the attendant disadvantages for the quality of the product already mentioned above. Furthermore, the process entails the loss of biuretizing agent and release of combustible gases (isobutene).

The reaction of the diisocyanates with aldoximes is also characterized by the loss of the difficultly accessible biuretizing agent and the occurrence of highly volatile by-products (nitriles) which cannot be reused.

The reaction of diisocyanates with hydrogen sulphides gives rise to the toxic, low-boiling product, carbon oxysulphide, which also cannot be returned to the process and must be removed by elaborate procedures.

Common to all the processes mentioned so far is the fact that part of the diisocyanate is converted by reaction with the biuretizing agent into amines, i.e. the precursors of isocyanates. Processes have therefore been proposed for the direct conversion of diisocyanates to biuret polyisocyanates by reaction with amines.

However, due to the high reactivity of amines, these processes are accompanied by the formation of difficultly soluble polyureas even when highly developed mixing processes are employed, so that considerable application of heat is again necessary to dissolve these polyureas, and the high temperatures employed result in a deterioration in the color quality and increased formation of by-products. Not only uretdiones and isocyanurates but also carbodiimides and secondary products of carbodiimides are formed which have an adverse effect on the monomer stability of the end product.

The tendency to the formation of difficultly soluble polyureas may be reduced by the use of diamines whose reactivity has been significantly reduced by suitable means, e.g. by steric hindrance. The products, however, contain inter alia a high proportion of monomeric diisocyanates which have been formed from the diamines put into the process and cannot be removed by thin layer distillation.

Although the use of $\omega,\omega'$-diaminopolyethers gives rise to liquid polyisocyanates containing biuret, this solution to the problem is very expensive owing to the additional synthesis of biuretizing agent. Moreover, the ether groups present in these products result in poor weather resistance of the lacquer films obtained from them.

The formation of polyureas may be avoided by using monoamines or N,N'-disubstituted ureas, but the highly volatile monoisocyanates formed from these biuretizing agents must be removed from the reaction mixture. This can only be incompletely achieved, even at a high temperature, owing to the inevitable equilibrium reactions.

Although products with good color quality may be produced under mild conditions when diisocyanates are reacted with formic acid, these products still contain a high proportion of N-formyl groups. In order to obtain a polyisocyanate having a predominantly biuret structure, it is necessary to employ reaction temperatures of more than 160° C. over a considerable time, thus causing a marked yellow discoloration. Moreover, the biuretizing agent is used up with the release of toxic carbon monoxide, causing considerable problems of effluent air disposal.

A process using diisocyanates and mixtures of amines and alcohols has also been proposed. Apart from other disadvantages, the products obtained from such processes are modified in their structure and have different properties. The same applies to products obtained from processes in which diisocyanates are reacted with ammonia.

It has now been found that polyisocyanates with biuret structure can be obtained with excellent color quality and good monomer stability by the reaction of aliphatic diisocyanates with certain monocarboxylic acids described in more detail below at comparatively low temperatures if the reactants are used in certain proportions.

SUMMARY OF THE INVENTION

The present invention relates to a process for the preparation of polyisocyanates which have a biuret structure by reacting excess quantities of aliphatic diisocyanates with biuretizing agents at elevated temperature, characterized in that the biuretizing agent contains
(a) $\alpha,\alpha,\alpha$-trisubstituted aceric acids which do not contain isocyanate-reactive groups apart from the carboxyl group, and optionally
(b) water,
wherein the molar ratio of biuretizing components (a) to (b) is within the range of from 1:0 to 1:2.5.

DETAILED DESCRIPTION OF THE INVENTION

The aliphatic diisocyanates used for the process according to the invention are linear or branch chained diisocyanates having 4–30, preferably 5–12 carbon atoms in the hydrocarbon group and optionally also having one or more ester groups. The following are mentioned as examples: 1,4-diisocyanatobutane, 1,5-diisocyanatopentane, 1,6-diisocyanatohexane, 1,8-diisocyanatooctane, 1,10-diisocyanatodecane, an isomeric mixture of 2,2,4-trimethyl-1,6-diisocyanatohexane and 2,4,4-trimethyl-1,6-diisocyanatohexane, 2-methyl-1,5-diisocyanatopentane, 2,2-dimethyl-diisocyanatopentane, 6-isocyanatohexanoic acid-(2-isocyanatoethyl)-ester and 2,6-bis-(isocyanato)-hexanoic acid methyl ester. 1,6-Diisocyanatohexane is particularly preferred as starting diisocyanate. The starting diisocyanates used may be of general commercial quality, no previous purification or tempering being required.

The term "biuretizing agent" is used in the context of this invention to mean organic compounds which react with isocyanate groups at elevated temperatures to form biurets. Thus, for example tert.-butanol is a biuretizing agent well known in the art. Essential to this invention is the use of (a) certain trisubstituted acetic acids, optionally in combination with (b) water, as biuretizing agents.

The $\alpha,\alpha,\alpha$-trisubstituted acetic acids suitable as biuretizing component (a) may be any trisubstituted acetic acids which have no hydrogen attached to the $\alpha$-carbon atom and contain no isocyanate reactive group apart from the carboxyl group. Examples of suitable $\alpha,\alpha,\alpha$-trisubstituted acetic acids include compounds of the general formula

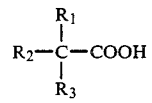

wherein $R_1$, $R_2$ and $R_3$ may be identical or different and denote alkyl, alkoxy or alkoxyalkyl groups, and two of the groups may form a cycloaliphatic ring together with the substituted carbon atom of the acetic acid, and the sum of the number of carbon atoms present in the groups $R_1$, $R_2$ and $R_3$ is preferably 3 to 6.

Suitable acids are, for example, 2,2-dimethyl-butyric acid; 2,2,3-trimethyl-butyric acid; 2-methyl-2-methoxymethylpropionic acid: 1-methyl-cyclopropane carboxylic acid and in particular trimethylacetic acid (pivalic acid). Methacrylic acid is also a suitable $\alpha,\alpha,\alpha$-trisubstituted acetic acid for the purpose of this invention since it satisfies the above condition that the $\alpha$-carbon atom of the acetic acid should not be linked to a hydrogen atom.

In the interests of obtaining an economical process, the acids to be used according to the invention should advantageously fulfill certain conditions. They should be readily accessible and the anhydrides formed from them should have a sufficiently different boiling point from that of the diisocyanate used to enable them to be removed from the reaction mixture by distillation before thin layer evaporation is carried out. If the isocyanate component used is the preferred 1,6-diisocyanatohexane, then this requirement is fulfilled, for example, by pivalic acid and 2,2-dimethyl butyric acid. However, anhydrides of other α,α,α-trisubstituted acetic acids boil at the same or at a higher temperature than 1,6-diisocyanatohexane and, therefore, if they are to be separated and used again after hydrolysis, an additional distillation is required after the excess diisocyanate and acid anhydride have been together removed from the reaction mixture by thin layer evaporation. Since, moreover, pivalic acid is commercially available, it is preferred for the process according to the invention.

In the process according to the invention, the α,α,α-trisubstituted acetic acids mentioned as examples may be used as the only biuretizing agents. According to a second variation of the process of the invention, the biuretizing agents according to the invention are used in combination with water so that the biuretizing agent is the combination of substituted acetic acid and water. The biuretizing agents (a) and optionally (b) are used in a molar ratio of acid:water in the range of from 1:0 to 1:2.5, preferably from 1:0 to 1:1.5. The total quantity of biuretizing agent used corresponds here to a molar ratio of starting diisocyanate:"total water" of from about 3:1 to 20:1, preferably from about 5:1 to 12:1, where "total water" denotes both the water optionally added as biuretizing component (b) and the water of condensation which would theoretically be formed if the trisubstituted acetic acid put into the process were quantitatively converted into its anhydride with elimination of water. The quantity "1 mol of water" thus corresponds, based on the trisubstituted acetic acids which are to be regarded as water releasing compounds, to the quantity "2 mol of trisubstituted acetic acid."

It would theoretically also be conceivable to use other biuretizing agents of known type in addition to the biuretizing agents used according to the invention. This, however, would result in no improvement to the process or to the products of the process.

It may be advantageous, in particular when water is used, to carry out the process according to the invention in the presence of a solvent which is at least to some extent miscible with water and inert towards isocyanates and acids. The following are mentioned as examples of solvents which may be used: ethers such as diisopropylether, ethylene glycol dimethylether, diethyleneglycol dimethylether, 1,4-dioxane, tetrahydrofuran and 1,2-dimethoxypropane; esters such as butyrolactone, ethylene glycol carbonate and propylene glycol carbonate; ether esters such as methoxyethylacetate, ethoxyethylacetate, 1-methoxypropyl-2-acetate, 2-methoxypropyl-1-acetate, 1-ethoxypropyl-2-acetate and 2-ethoxypropyl-1-acetate; ketones such as acetone and methyl ethyl ketone; nitriles such as acetonitrile, propionitrile and methoxypropionitrile; sulphones such as sulpholane, dimethylsulphone and diethylsulphone; phosphoric acid esters such as triethyl-/trimethylphosphate.

The following are less preferred solvents: tetramethylurea, N-methylpyrrolidone, dimethylformamide and dimethylacetamide.

The process according to the invention is carried out at temperatures of about 20° to 160° C., preferably about 60° to 140° C.

The process is usually carried out at normal pressure but it may, of course, also be carried out at pressures of from about 1 to 50 bar, preferably about 1 to 5 bar, especially when water and/or low boiling solvents are used.

The main product of the reaction of isocyanates with carboxylic acid is normally stated in the literature to be carboxylic acid amide:

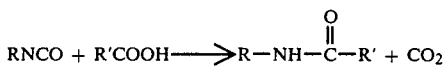

It is only in some literature references that the intermediate formation of mixed anhydrides is described; these are thermally unstable and decompose into the amide with elimination of carbon dioxide. In the case of a few isocyanates, there has also been described another path of decomposition, in which the anhydride formed is partially decomposed with the formation of urea and carboxylic acid anhydride.

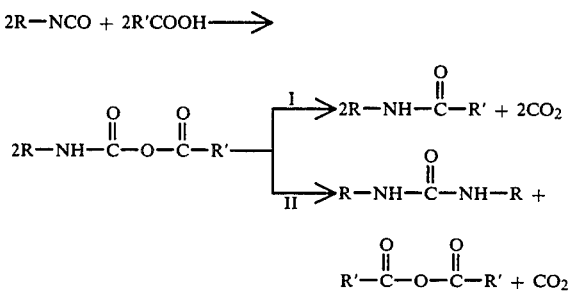

When aliphatic diisocyanates are used, however, decomposition into the carboxylic acid amide is found to be predominant.

In the presence of excess isocyanate, the urea formed along path II may continue to react with isocyanate to form biurets or it may be acylated by the anhydride formed.

It is described in DE-AS No. 1,174,760 that when formic acid is used as carboxylic acid, biurets alone are obtained with elimination of carbon monoxide as the anhydride of formic acid. However, later work on this subject and the teaching of DE-OS No. 2,308,015 disclose that a very large proportion of N-formylurea groups must be present instead of biuret groups in the products of DE-AS No. 1,174,760. Another indication of this is Example 1 of DE-AS No. 1,174,760 (column 3, line 51 to column 4, line 10). Both the isocyanate content found and the viscosity of 853 mPas at 25° C. of the products described there show unequivocally that a large quantity of N-formylureas must be present. In a reaction mixture having the composition described there, a polyisocyanate having an exclusively biuret structure would have to have an isocyanate content of about 22.8% and a viscosity of about 7000 mPas at 25° C.

Our own experiments (see Comparison Example 1) clearly confirm this. The product composition was examined by gel chromatography and it was found that the ratio of biuret groups to formylureas in the products was in the region of about 1:3 to 3:1, depending upon the reaction conditions, and the products having the larger quantities of biuret groups also contained a considerable quantity of by-products such as uretdiones and were strongly colored.

It has now surprisingly been found that when excess aliphatic diisocyanates of the type mentioned above are reacted with α,α,α-trisubstituted acetic acids, the reaction leads almost exclusively to the formation of carboxylic acid anhydrides and the intermediate formation of urea, and that the urea formed as intermediate product reacts rapidly and quantitatively in the presence of the excess diisocyanate at temperatures at which N,N'-dialkyl substituted ureas normally do not yet react or react only much more slowly with isocyanates.

It has furthermore surprisingly been found that in the presence of the acids according to the invention, the formation of biurets from diisocyanates and water proceeds much more rapidly and at lower temperatures than in the absence of these acids. The acid apparently acts as a carrier, in that the water put into the process hydrolyzes the acid anhydride formed so that the acid is formed again.

Formic acid cannot function as carrier in the sense described above since it forms carbon monoxide as internal anhydride, from which the formic acid, of course, cannot be formed back by reaction with water under the reaction conditions.

Other acids, e.g. acetic acid, can produce the above described effect only to a limited extent since they mainly react to form carboxylic acid amides with evolution of carbon dioxide and since these carboxylic acid amides cannot be hydrolyzed under the reaction conditions, the acids rapidly disappear from the reaction mixture.

Due to the reformation of the acids according to the invention from water and anhydride, the process according to the invention can still be carried out when biuret formation is formally brought about partly by $\alpha,\alpha,\alpha$-trisubstituted acetic acid and partly by water. Mixtures of acids with water may therefore be used as biuretizing agents according to the invention for the preparation of polyisocyanates having a biuret structure.

The process according to the invention may be carried out, for example, as follows:

The diisocyanate to be used is introduced at room temperature into a stirred reactor optionally equipped with a measuring device for the carbon dioxide formed.

The acid is dosed into the diisocyanate in the course of about 30 minutes from a receiver which is optionally equipped to be heated so that acids which are solid at room temperature may be used in molten form. Exothermic formation of the mixed anhydride from isocyanate and acid sets in, while the reaction mixture is heated to about 50° C. Evolution of gas begins at a moderate rate at this temperature and is then continued at an acceptable velocity by heating to 60°-80° C. When the evolution of gas decreases towards the end of the reaction, the reaction mixture is heated to 100°-120° C. The total time required for the reaction is 2 to 4 hours.

The reaction may, of course, also be carried out at lower temperatures, e.g. at room temperature if the reaction heat of the primary reaction between diisocyanate and water is removed by some suitable means. The reaction then takes several days for completion. When these temperatures are employed, however, cloudiness initially appears and must be redissolved by subsequent prolonged heating at 120° to 140° C.

The diisocyanate may, of course, be introduced into the reaction vessel as a mixture with a solvent at an elevated temperature of 80° to 120° C, acid and optionally water being then added as the reaction progresses. This method would be advantageous in cases where water is used, in which case a higher initial temperature should be employed to avoid the formation of difficultly soluble urea precipitates, the initial temperature required increasing with the water content of the biuretizing agent.

When the acids according to this invention are used as the only biuretizing agent, the reaction mixtures are substantially homogeneous and the use of a solvent is normally not necessary and affords no advantages. If, however, a portion of the biuret groups is produced by reaction of water with diisocyanate, the carbon dioxide evolved may carry the water with it, and this water may then condense in the upper part of the reaction vessel or enter the exhaust air and be thus removed from the reaction. These uncontrolled losses of water may be prevented by the addition of a solvent which has a suitable boiling point and is at least partly miscible with water.

Another advantage of using a solvent is that it enables a more homogeneous reaction mixture to be obtained when water is also used, so that the reaction velocity is increased. The quantities of solvent required for this purpose are distinctly lower than, for example, the quantities normally used in the process according to DE-OS No. 2,808,801, and generally correspond to 3-20% by weight of the diisocyanate put into the process. One reason why these quantities may be kept so low is that complete homogeneity of the reaction mixture, which is necessary for the process according to DE-OS No. 2,808,801, is not necessary due to the alternative path of reaction for the process according to the invention.

The solvent optionally used may be partly or completely introduced together with the diisocyanate or it may be partly or completely added to the diisocyanate with the acid and any water used. The acid and water may be introduced either separately or together, and optionally as a mixture with solvents.

When water and/or solvents are used, it may be advantageous to operate under excess pressure to prevent loss of these components. The maximum pressure during the reaction is advantageously limited to 6 bar by suitable means, e.g. by an excess pressure valve, since up to that pressure there is no difficulty in using ordinary technical apparatus. The reaction may also be carried out at higher pressures, e.g. under the full pressure of carbon dioxide developed during the reaction, in which case pressures of up to a maximum of 20 bar may occur depending upon the temperature and the degree to which the reactor is filled. In such cases, however, it is necessary to use special high pressure apparatus.

The proportion of isocyanate groups to acid and water may be varied within wide limits, as already mentioned above. It determines the oligomer distribution of the resulting biuret polyisocyanate and hence important properties of the product, e.g. isocyanate content and viscosity. Thus, two biuret polyisocyanates having viscosities of 10,000 mPas and 2500 mPas at 23° C. were obtained according to the process of this invention when molar ratios of isocyanate groups to the "total water" of an acid or acid/water mixture of 11/3 and 6/1, respectively, are used to form biurets.

End products having an even lower viscosity may, of course, be prepared by using larger excesses of isocyanate. However, due to the increased distillation work required, the lower volume/time yield and the increased formation of by-products, the process rapidly becomes uneconomical. At the same time, the range of variation is limited by the formation of products with extremely high viscosities which progressively become incompatible with the nonpolar solvents used with polyisocyanates. When more than half the isocyanate groups of the diisocyanate originally present undergo reaction, the formation of insoluble gels must, of course, be expected.

After termination of the reaction excess diisocyanate, carboxylic acid anhydride and any solvents present are removed from the reaction mixture by distillation. If no solvent was used and the acid anhydride formed has a lower boiling point than the diisocyanate, it is advantageous first to remove most of the acid anhydride from the reaction mixture by distillation under vacuum. In practice, about 90% of the anhydride present in the reaction mixture may effortlessly be isolated in pure form, free from diisocyanate. The residual anhydride thus remains in the reaction mixture and is separated from the biuret polyisocyanate by a thin layer distillation, together with the excess diisocyanate. Since the anhydride left in the excess diisocyanate has no harmful effect on the process according to the invention, the mixture obtained may be directly returned to the process.

It is also theoretically possible, although less preferred, to separate the excess diisocyanate from the resulting biuret polyisocyanate by extraction with suitable solvents such as n-hexane, for example, after removal of the solvent and the acid anhydride.

The previously separated anhydride may easily be hydrolyzed to the acid by heating with water and used again. Since the process according to the invention may also be carried out with mixtures of acid and water, complete hydrolysis of the separated anhydride is not absolutely necessary.

The method of completely removing the acid anhydride from the reaction solution by distillation results in a product which is contaminated with diisocyanate and in which difficultly soluble carboxylic acid amides are formed on hydrolysis. To prevent these precipitations, another distillation would be necessary and, thus, this method is less preferred.

If the anhydride of the carboxylic acid used boils at a higher temperature than the diisocyanate put into the process, the two are removed together by thin layer distillation, so that a further distillation step is necessary if the acid is to be recovered.

This method is therefore also less preferred. Accordingly, it is advantageous to use acids whose anhydrides have a lower boiling point than the diisocyanates used.

If a solvent is also used, this may be removed from the reaction mixture, either separately or together with the anhydride or together with excess diisocyanate, depending upon its boiling point, and used again. If it is isolated together with the acid anhydride formed, subsequent hydrolysis of the anhydride does not require separation of the solvent. The use of a solvent/anhydride mixture for hydrolysis may even be advantageous since the solvent acts as solubilizing agent between water and the anhydride, which may in some cases be immiscible with water.

The process is, of course, eminently suitable for being conducted by a continuous process. In that case, diisocyanate and carboxylic acid, optionally together with water and/or a solvent, may be introduced separately or as a mixture, for example into the first of 4 to 6 stirred reactors arranged as a cascade, the substances being added at such a rate that a residence time of 2 to 8 hours is obtained prior to leaving the last reactor. The temperature in the individual reactors may be uniformly 100° to 140° C. or increase from 60° to 140° C., preferably from 80° to 120° C.

Depending upon the boiling points of the diisocyanate, the acid anhydride formed and the solvent, if used, the reaction mixture may either be initially passed through a continuously operating distillation column to remove the anhydride, optionally together with the solvent, and the biuret polyisocyanate may subsequently be freed from excess diisocyanate and residues of anhydride and any solvent present by thin layer distillation or extraction. Alternatively, the biuret polyisocyanate may first be freed from excess diisocyanate, anhydride and solvent by thin layer evaporation, and the evaporation product may then be separated into diisocyanate and anhydride through a column, and any solvent used may be removed either separately or together with one of the other components. The anhydride thus obtained, optionally as a mixture with solvent, is subsequently hydrolyzed to the acid either completely or partially, continuously or batchwise, and then, like the excess diisocyanate, is returned to the process.

In the preferred reaction of 1,6-diisocyanatohexane with pivalic acid, for example, the pivalic acid anhydride formed is first separated off through a column and hydrolyzed, and the biuret polyisocyanate is then freed from excess 1,6-diisocyanatohexane by thin layer evaporation.

The polyisocyanates with biuret structure prepared by the process according to the invention are distinguished by their high color quality and good storage stability and are substantially free from by-products. They are eminently suitable for the production of light-fast and extremely weather-resistant lacquers with excellent gloss retention.

The process according to the invention is explained in more detail in the Examples which follow.

The invention is further illustrated, but is not intended to be limited by the following examples in which all parts and percentages are by weight unless otherwise specified.

EXAMPLES

Example 1

6049 g (36 mol) of hexamethylene diisocyanate were introduced at 20° C. into a 10 l four-necked flask with contact thermometer, stirrer and reflux condenser, and 1224 g (12 mol) of molten pivalic acid were added with stirring. The temperature of the reaction mixture rose spontaneously to about 50° C., and slow evolution of $CO_2$ set in. The gas was removed through a bubble counter at the upper end of the condenser and controlled volumetrically by means of a gas meter. The temperature was raised to 80° C. in the course of 2 hours and then kept at this level for one hour. 130 l (standard conditions) (5.8 mol) of $CO_2$ had been released by the end of that time. Stirring was then continued for a further 30 minutes at 130° C. to complete the reaction which had by now slowed down so that no further $CO_2$ was evolved. The total quantity (standard conditions) was 136 l (6.07 mol). The reaction mixture was then cooled to 80° C., and pivalic acid anhydride was distilled off through a packed column (50 cm height, 5 cm diameter) at 10 mbar. A first fraction of 970 g (87% of theoretical) boiling at 81° C. was 99.9% pure. A second fraction (120 g) consisted of 89% pivalic acid anhydride and 11% hexamethylene diisocyanate. The total yield of anhydride was thus 1077 g (96.5% of theoretical yield).

The first fraction was heated to 100° C. with an equimolar quantity of water for 30 minutes and the pivalic acid thus obtained was used for subsequent reaction mixtures without further purification.

The crude biuret polyisocyanate obtained was water clear and free from any solid particles. Half the product (2985 g) was freed from excess diisocyanate by being subjected twice to thin layer distillation (150° C., 0.5 mbar). 1200 g of a biuret polyisocyanate having the following properties were obtained:
Isocyanate content: 22.5%
Viscosity at 25° C.: 6950 mPas
APHA color number (DIN 53 409): 30
Monomeric diisocyanate content: 0.3% by weight
After storage (6 weeks, 50° C.): 0.4% by weight.

The other half of the crude product was worked up by fractional extraction using n-hexane as solvent:
Yield: 1150 g
Isocyanate content: 22.3%
Viscosity at 25° C.: 7500 mPas
APHA color number: 20-30
Monomer content: 0.2% by weight.

Example 2

3024 g (18 mol) of hexamethylene diisocyanate were introduced into the reaction vessel at 120° C. and 408 g (4 mol) of pivalic acid were added dropwise in the course of 2 hours. Evolution of $CO_2$ was completed after a further hour at the same temperature. 91 l (standard conditions) (4.06 mol) were measured. Distillation at 20 mbar, sump temperature 100°–140° C., yielded 378 g, 94% of which was pivalic acid anhydride. Yield: 95.5% of theory. 860 g of a biuret polyisocyanate having the following properties were obtained after thin layer distillation.
Isocyanate content: 23.6%
Viscosity at 25° C.: 2540 mPas
APHA color number: 40
Monomer content: 0.15%
After storage (6 weeks, 50° C.): 0.23%.

Example 3

612 g (6 mol) of pivalic acid were added to 2520 g (15 mol) of hexamethylene diisocyanate. The temperature of the mixture was adjusted to 50° C. with a water bath. Weak evolution of gas set in. 28.5 l (standard conditions) (85% of theory) of $CO_2$ evolved in the course of 24 hours. A finely divided precipitate of urea intermediate products had formed. The reaction mixture was then heated to 140° C. in the course of 2 hours and stirred at this temperature for a further 2 hours. During this time, the precipitate dissolved completely with formation of biuret. The quantity of $CO_2$ increased to 33.8 l (standard conditions) (101% of theory). After removal of the pivalic acid anhydride by distillation at 20 mbar, excess hexamethylene diisocyanate was removed by thin layer distillation. 1180 g of a biuret polyisocyanate having the following properties were obtained:
Isocyanate content: 21.4%
Viscosity at 25° C.: 16200 mPas
APHA color number: 40
Monomer content: 0.23%.

Example 4

900 g of a biuret polyisocyanate having the following properties were obtained in the form of a thin liquid from 4032 g (24 mol) of hexamethylene diisocyanate and 408 g (4 mol) of pivalic acid by a procedure analogous to that of Example 2:
Isocyanate content: 24.4%
Viscosity at 25° C.: 1250 mPas
APHA color number: 35
Monomer content: 0.15%.

Comparison Example I 2016 g (12 mol) of hexamethylene diisocyanate were introduced into a reaction vessel and 92 g (2 mol) of formic acid were added using a method analogous to that of Example 1. The temperature, which initially rose to 50° C., was raised to 120° C. in the course of 2 hours and then kept at that level for a further 2 hours. The reaction was then completed. The quantity of gas was initially measured in a first gas meter and the stream of gas leaving this meter was conducted through two wash bottles filled with 20% sodium hydroxide solution into a second gas meter to determine the proportion of carbon monoxide. A total quantity of gas of 56.7 l (standard conditions) (2.53 mol) was measured. The proportion of carbon monoxide at standard conditions was 11.9 l (0.53 mol). The isocyanate content of the crude solution was 40.3%, corresponding to a consumption of 4.76 mol of NCO. From this result and from gas analysis and interpretation of gel chromatographic analyses, it was found that the reaction using formic acid yielded 73.5% of formylurea groups, but only 26.5% of biuret groups.

After thin layer distillation, 650 g of a modified isocyanate having the following properties were obtained from the crude solution:
Isocyanate content: 22.6%
Viscosity at 25° C.: 515 mPas
APHA color number: 50
Monomer content: 0.16%.

The gel chromatogram showed N-formyl-N,N'-bis-(isocyanatohexyl)-urea to be the main component, amounting to 48.5% by weight.

Comparison Example II

In this example, the isocyanate was introduced into the reaction vessel at 120° C. and formic acid was added dropwise within 2 hours. The following data was obtained:
Total gas quantity: 3.08 mol
Quantity of CO: 1.08 mol
Isocyanate content of crude solution: 39.3%
Isocyanate consumption: 5.43 mol
Biuret proportion: 54%
Formylurea proportion: 46%
After thin layer distillation:
Yield: 750 g
Isocyanate content: 22.6%
Viscosity at 25° C.: 1200 mPas
APHA color number: 70
Monomer content: 0.23%
Gel chromatogram: 28.5% by weight of the simple formylurea.

Comparison Example III

Hexamethylene diisocyanate was introduced into the reaction vessel at 160° C. and formic acid was added dropwise in the course of 2 hours. The following data were obtained:
Total gas quantity: 3.44 mol
Quantity of CO: 1.44 mol Isocyanate consumption: 6.04 mol
Biuret proportion: 72%
Formylurea proportion: 28%

In addition, according to gas analysis, gel chromatogram, IR spectrum and isocyanate consumption, the product contained 14% of uretdione groups.

After thin layer distillation:
Yield: 910 g
Isocyanate content: 21.9%
Viscosity at 25° C.: 1860 mPas
APHA color number: 200
Iodine color number: 1-2
Monomer content: 0.3%
Gel chromatogram: 19.5% by weight of the simple formylurea.

Comparison Example IV 1008 g (6 mol) of hexamethylene diisocyanate were reacted, in a manner analogous to Example 1, with 2 mol each of acetic acid, propionic acid and isobutyric acid.

| Quantity of $CO_2$ (mol) | 1.58 | 1.42 | 1.32 |
|---|---|---|---|
| Anhydride yield | 42% | 58% | 68% |
| Isocyanate content of the crude solution | 33.6% | 33.1% | 32.5% |
| Isocyanate consumption (mol) | 3.58 | 3.42 | 3.32 |
| Iodine color number of the crude solution | 5-6 | 2-3 | 1-2 |

In view of the high color numbers of the crude products and the low anhydride yields, the reaction mixtures were not worked up.

Comparison Example V 500 g of a crude biuret solution obtained by a method analogous to that of Example 1 were heated to 140° C. together with 102 g (1 mol) of acetic anhydride. The reaction mixture discolored after a short time and a small evolution of gas sets in. 13% of the anhydride put into the process were used up after 3 hours. After a further 2 hours at 160° C., the anhydride consumption amounted to 53.3%. The mixture was a deep red color.

When instead of acetic anhydride, the equivalent quantity of pivalic acid anhydride was used, no change in the reaction mixture was found after the same temperature treatment and the anhydride could be distilled off quantitatively.

Example 5

630 g (3 mol) of trimethylhexane diisocyanate (isomer mixtures of 2,2,4- and 2,4,4-) were reacted with 126 g (1 mol) of 2,2,3-trimethyl-butyric acid in a manner analogous to Example 2. The calculated quantity (0.5 mol) of $CO_2$ was released, and 109 g of the corresponding acid anhydride were distilled off at 0.1 mb (b.p. 60° to 64° C.).

250 g of a viscous biuret polyisocyanate having the following properties were obtained after thin layer distillation:
Isocyanate content: 18.3%
Viscosity at 25° C.: 97,500
APHA color number: 30
Monomer content: 0.4%.

Example 6

2016 g (12 mol) of 3-methylpentane-1,5-diisocyanate were introduced into a reaction vessel at 80° C. 200 g (2 mol) of 1-methyl-cyclopropane-carboxylic acid and 18 g (1 mol) of distilled water were added dropwise simultaneously from two separate dropping funnels in the course of 2 hours.

After addition of these components had been completed, the reaction mixture was stirred for a further 30 minutes at 100° C. and 30 minutes at 120° C. Evolution of $CO_2$ was then completed. A fraction of 320 g was then distilled off at 2 mbar. According to gas chromatography and isocyanate determination, this fraction contained 52.9% of the acid anhydride (93% of theory) and 47.0% of the diisocyanate put into the process.

810 g of a biuret polyisocyanate having the following properties were obtained after thin layer distillation:
Isocyanate content: 22.5%
Viscosity at 25° C.: 31,900 mPas
APHA color number: 20-30
Monomer content: 0.3%.

Example 7

6048 g (36 mol) of hexamethylene diisocyanate and 300 ml of 1,4-dioxane were introduced into a reaction vessel at 100° C. and a solution of 155 g (1.33 mol) of 2,2-dimethyl-butyric acid and 60 g (3.3 mol) of distilled water in 200 ml of 1,4-dioxane was added dropwise in the course of 3 hours. Evolution of gas (4 mol) was completed after a further hour at 130° C. The solvent was then drawn off at 50 mbar and a fraction (200 g) was distilled off at 15 mbar. After redistillation, this fraction yielded 123 g of the pure acid anhydride (b.p. 118/15 mbar) (94% of theory). Subsequent thin layer distillation yielded 1730 g of a low viscosity biuret polyisocyanate having the following properties:
Isocyanate content: 23.6%
Viscosity at 25° C.: 2350 mPas
APHA color number: 30
Monomer content: 0.18%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanates having a biuret structure by reacting excess quantities of an aliphatic diisocyanate at elevated temperature with a biuretizing agent based on
   (a) an α,α,α-trisubstituted acetic acid containing no isocyanate reactive groups apart from the carboxyl group and optionally
   (b) water,
wherein the molar ratio of component (a) to component (b) is from 1:0 to 1:2.5.

2. The process of claim 1 wherein said aliphatic diisocyanate is 1,6-diisocyanatohexane.

3. The process according to claim 1 wherein said α,α,α-trisubstituted acetic acid corresponds to the formula

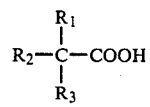

in which $R_1$, $R_2$ and $R_3$ may be identical or different and denote alkyl, alkoxy, or alkoxyalkyl groups, wherein optionally two of the groups together with the substituted carbon atom of the acetic acid form a cycloaliphatic ring.

4. The process according to claim 2 wherein said α,α,α-trisubstituted acetic acid corresponds to the formula

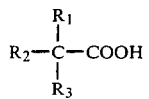

in which $R_1$, $R_2$ and $R_3$ may be identical or different and denote alkyl, alkoxy, or alkoxyalkyl groups, wherein optionally two of the groups together with the substituted carbon atom of the acetic acid form a cycloaliphatic ring.

5. The process of claim 1 wherein said α,α,α-trisubstituted acetic acid is trimethyl acetic acid.

6. The process of claim 2 wherein said α,α,α-trisubstituted acetic acid is trimethyl acetic acid.

7. The process of claim 1 wherein said process is conducted in the presence of a water-miscible solvent.

8. The process of claim 1 wherein excess quantities of said aliphatic diisocyanate and the anhydride of component (a) are removed from the biuret polyisocyanate product by distillation and/or extraction after the biuretization reaction.

* * * * *